(12) United States Patent
Naito et al.

(10) Patent No.: US 9,836,830 B2
(45) Date of Patent: Dec. 5, 2017

(54) RADIOGRAPHIC IMAGE PROCESSING DEVICE, METHOD, AND RECORDING MEDIUM

(71) Applicant: FUJIFILM Corporation, Tokyo (JP)

(72) Inventors: Satoshi Naito, Ashigarakami-gun (JP); Takahiro Kawamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 29 days.

(21) Appl. No.: 15/160,053

(22) Filed: May 20, 2016

(65) Prior Publication Data

US 2016/0267630 A1    Sep. 15, 2016

Related U.S. Application Data

(63) Continuation of application No. PCT/JP2014/005857, filed on Nov. 21, 2014.

(30) Foreign Application Priority Data

Nov. 26, 2013 (JP) .................................. 2013-243513

(51) Int. Cl.
*G06K 9/00* (2006.01)
*G06T 5/00* (2006.01)
(Continued)

(52) U.S. Cl.
CPC ............ *G06T 5/008* (2013.01); *A61B 6/5211* (2013.01); *A61B 6/5282* (2013.01);
(Continued)

(58) Field of Classification Search
CPC ..................................................... G06K 9/00
See application file for complete search history.

(56) References Cited

U.S. PATENT DOCUMENTS 5,465,147 A * 11/1995 Swanson ............ A61B 1/00183
356/497
5,467,404 A    11/1995 Vuylsteke et al.
(Continued)

FOREIGN PATENT DOCUMENTS

JP    5-244508 A    9/1993
JP    6-292009 A    10/1994
(Continued)

OTHER PUBLICATIONS

John M Boone et al., "An Analytical model of the scattered radiation distribution in diagnostic radiology", Med. Phys., Sep./Oct. 1988, pp. 721-725, vol. 15, No. 5.
(Continued)

*Primary Examiner* — Anand Bhatnagar
(74) *Attorney, Agent, or Firm* — Sughrue Mion, PLLC

(57) ABSTRACT

A frequency resolution unit performs frequency resolution of a radiographic image to generate band images representing frequency components in a plurality of frequency bands. A reference image generation unit generates a reference image representing information associated with scattered radiation included in the radiographic image, and generates a plurality of band reference images corresponding to a plurality of frequency bands from the reference image. A band image conversion unit performs conversion between the corresponding pixels of the band reference images and the band images in the corresponding frequency bands to generate converted band images. A synthesis unit synthesizes the converted band images to generate a processed radiographic image with converted contrast.

10 Claims, 13 Drawing Sheets

(51) Int. Cl.
*A61B 6/00* (2006.01)
*G01N 23/04* (2006.01)
*G06T 5/10* (2006.01)

(52) U.S. Cl.
CPC ............. *G01N 23/046* (2013.01); *G06T 5/10* (2013.01); *G06T 2207/10116* (2013.01); *G06T 2207/20016* (2013.01); *G06T 2207/30061* (2013.01)

(56) References Cited

U.S. PATENT DOCUMENTS

| | | | |
|---|---|---|---|
| 5,493,622 A | 2/1996 | Tsuchino et al. | |
| 5,805,721 A | 9/1998 | Vuylsteke et al. | |
| 5,960,058 A | 9/1999 | Baba et al. | |
| 6,014,214 A * | 1/2000 | Li | G01N 21/4795 356/511 |
| 7,165,353 B2 * | 1/2007 | Matts | A01M 1/026 43/131 |
| 8,064,676 B2 * | 11/2011 | Li | A61B 6/00 382/132 |
| 8,417,048 B2 * | 4/2013 | Reboni | G06T 5/002 382/132 |
| 2003/0161548 A1 * | 8/2003 | Vuylsteke | G06T 5/009 382/274 |
| 2004/0101106 A1 * | 5/2004 | Inoue | G01T 1/2928 378/154 |
| 2010/0046822 A1 * | 2/2010 | Li | A61B 6/00 382/132 |
| 2012/0008849 A1 * | 1/2012 | Reboni | G06T 5/009 382/132 |
| 2013/0223717 A1 * | 8/2013 | Reboni | G06T 7/0012 382/131 |
| 2015/0075060 A1 * | 3/2015 | Balsam | A01M 1/026 43/123 |
| 2015/0366210 A1 * | 12/2015 | Olson | A01M 1/026 43/112 |

FOREIGN PATENT DOCUMENTS

| | | |
|---|---|---|
| JP | 9-149895 A | 6/1997 |
| JP | 2001-218058 A | 8/2001 |
| JP | 2003-319261 A | 11/2003 |
| JP | 2012-518858 A | 8/2012 |
| WO | 2011/058612 A1 | 5/2001 |

OTHER PUBLICATIONS

Christiaan Fivez et al., "Multi-Resolution Contrast Amplification in Digital Radiography with Compensation for Scattered Radiation", IEEE, 1996, pp. 339-342, vol. 1.
International Search Report for PCT/JP2014/005857 dated Mar. 10, 2015, English Translation.
Written Opinion for PCT/JP2014/005857 dated Mar. 10, 2015, Partial English Translation.

* cited by examiner

RADIOGRAPHIC IMAGE PROCESSING DEVICE, METHOD, AND RECORDING MEDIUM

CROSS-REFERENCE TO RELATED APPLICATIONS

This application is a Continuation of PCT International Application No. PCT/JP2014/005857 filed on Nov. 21, 2014, which claims priority under 35 U.S.C. §119(a) to Japanese Patent Application No. 2013-243513 filed on Nov. 26, 2013. Each of the above applications is hereby expressly incorporated by reference, in its entirety, into the present application.

BACKGROUND OF THE INVENTION

1. Field of the Invention

The present invention relates to a radiographic image processing device and method and a radiographic image processing program which perform image processing for converting contrast of a radiographic image.

2. Description of the Related Art

Various methods for improving contrast of a radiographic image acquired by exposing an object to radiation have been hitherto suggested. For example, JP1993-244508A (JP-H05-244508A) suggests a method which performs frequency resolution of a radiographic image to generate band images in a plurality of frequencies, converts contrast of the band images of the respective frequency bands using a nonlinear function, and performs frequency synthesis of the converted band images to acquire a radiographic image with converted contrast. JP2001-218058A suggests a method which converts contrast of the band images using a function for making the degree of enhancement in a low contrast region for a band image of a comparatively high frequency band among the band images greater than the degree of enhancement in a low contrast region for a band image of a comparatively low frequency band to acquire a radiographic image with converted contrast.

SUMMARY OF THE INVENTION

On the other hand, there is a problem in that, when capturing a radiographic image of an object, radiation is scattered in the object, and contrast of the radiographic image to be acquired is degraded due to scattered radiation. In this case, it is considered that a filter simulating scattered radiation is created from the radiographic image, and the filter is applied to each pixel on the radiographic image to eliminate scattered radiation from the radiographic image, thereby improving contrast of the radiographic image. However, since scattered radiation has deviation in the frequency band, it is not possible to appropriately eliminate scattered radiation with deviation in the frequency band by just performing filtering to the radiographic image. For this reason, it is considered that contrast of the band images is converted using a function according to the method described in each of JP1993-244508A (JP-H05-244508A) and JP2001-218058A to improve contrast.

However, since scattered radiation is also affected by the structure in the object, the distribution of scattered radiation is different at each position on the radiographic image. For this reason, it is difficult to appropriately eliminate the effect of scattered radiation by just converting contrast of the band images using the function as described in JP1993-244508A (JP-H05-244508A) and JP2001-218058A.

The invention has been accomplished in consideration of the situation described above, and an object of the invention is to improve degradation of contrast due to the effect of scattered radiation in a radiographic image.

A radiographic image processing device according to the invention comprises frequency resolution means for performing frequency resolution of a radiographic image captured by irradiating an object with radiation to generate band images representing frequency components in a plurality of frequency bands, reference image generation means for generating a reference image representing information associated with scattered radiation included in the radiographic image from the radiographic image and generating a plurality of band reference images corresponding to the plurality of frequency bands from the reference image, band image conversion means for performing conversion between the corresponding pixels of the band reference images and the band images in the corresponding frequency bands to generate converted band images, and synthesis means for synthesizing the converted band images to generate a processed radiographic image with converted contrast.

The "reference image" is an image in which information associated with scattered radiation is mapped as the pixel value of each pixel, and information associated with scattered radiation is obtained from the reference image for each pixel on the image. The "reference image" may have any format as long as the format can correspond to the coordinates of each pixel of the radiographic image or each band image.

"Performing conversion between the corresponding pixels of the band reference images and the band images" means, for example, multiplying the pixel values of the band images by the pixel values of the band reference images in the corresponding pixels of the band reference images and the band images or using the pixel values of the band reference images as parameters of nonlinear processing applied to the band images.

In the radiographic image processing device according to the invention, the reference image may be at least one of an image representing a body thickness distribution of the object, an image representing a scattered radiation content distribution of the radiographic image, an image representing a scattered radiation content according to an anatomical region included in the radiographic image, or an image representing a primary radiation content distribution of the radiographic image.

In the radiographic image processing device according to the invention, the reference image generation means may be means for generating a lowest frequency band reference image corresponding to the band image of a lowest frequency band and sequentially enlarging the lowest frequency band reference image to generate band reference images of the plurality of frequency bands including the lowest frequency band reference image.

The radiographic image processing device according to the invention may further comprise weight determination means for determining weights to the converted band images in the plurality of frequency bands, and the synthesis means may be means for generating the processed radiographic image based on the converted band images weighted by the weights.

In this case, the synthesis means may be means for weighting the converted band images by the weights and synthesizing the weighted converted band images to generate the processed radiographic image.

In this case, the band image conversion means may be means for weighting the band reference images by the weights.

The radiographic image processing device according to the invention may further comprise nonlinear conversion means for converting the band images with a nonlinear function, and the band image conversion means may be means for performing conversion between the corresponding pixels of the band reference images and the converted band images to generate the converted band images.

Another radiographic image processing device according to the invention comprises frequency resolution means for performing frequency resolution of a radiographic image captured by irradiating an object with radiation to generate band images representing frequency components in a plurality of frequency bands, reference image generation means for generating a reference image representing a primary radiation content distribution included in the radiographic image from the radiographic image and generating a plurality of band reference images corresponding to the plurality of frequency bands from the reference image, band image conversion means for performing conversion between the corresponding pixels of the band reference images and the band images in the corresponding frequency bands to generate converted band images, and synthesis means for synthesizing the converted band images to generate a processed radiographic image with converted contrast.

A radiographic image processing method according to the invention comprises performing frequency resolution of a radiographic image captured by irradiating an object with radiation to generate band images representing frequency components in a plurality of frequency bands, generating a reference image representing information associated with scattered radiation included in the radiographic image from the radiographic image and generating a plurality of band reference images corresponding to the plurality of frequency bands from the reference image, performing conversion between the corresponding pixels of the band reference images and the band images in the corresponding frequency bands to generate converted band images, and synthesizing the converted band images to generate a processed radiographic image with converted contrast.

The invention may also be provided as a program which causes a computer to execute the radiographic image processing method according to the invention.

According to the invention, the band images are generated from the radiographic image, the reference image representing information associated with scattered radiation included in the radiographic image is generated from the radiographic image, and a plurality of band reference images corresponding to a plurality of frequency bands are generated from the reference image. Then, conversion is performed between the corresponding pixels of the band reference images and the band images in the corresponding frequency bands to generate the converted band images, and the converted band images are synthesized to generate the processed radiographic image with converted contrast. For this reason, it is possible to eliminate the effect of scattered radiation in each frequency band and to eliminate the effect of scattered radiation at each position on the radiographic image. Therefore, it is possible to satisfactorily improve degradation of contrast due to the effect of scattered radiation in the radiographic image.

The lowest frequency band reference image corresponding to the band image in the lowest frequency band is generated, and the lowest frequency band reference image is sequentially enlarged to generate the band reference images of a plurality of frequency bands including the lowest frequency band reference image, whereby it is possible to reduce the calculation amount for generating the band reference images compared to a case where a reference image corresponding to a band image in a highest frequency band is generated; thus, it is possible to generate the reference image and the band reference image at high speed.

The weights to the converted band images in a plurality of frequency bands are determined, and the processed radiographic image is generated based on the converted band images weighted by the weights, whereby it is possible to vary the degree of elimination of scattered radiation in the respective frequency bands; thus, it is possible to appropriately eliminate the effect of scattered radiation according to deviation in the frequency band of scattered radiation. Therefore, it is possible to more satisfactorily improve degradation of contrast due to the effect of scattered radiation in the radiographic image.

The band images are converted with the nonlinear function, and conversion is performed between the corresponding pixels of the band reference images and the converted band images to generate the converted band images, whereby it is possible to improve contrast of the processed radiographic image.

DESCRIPTION OF THE PREFERRED EMBODIMENTS

Figure 1:
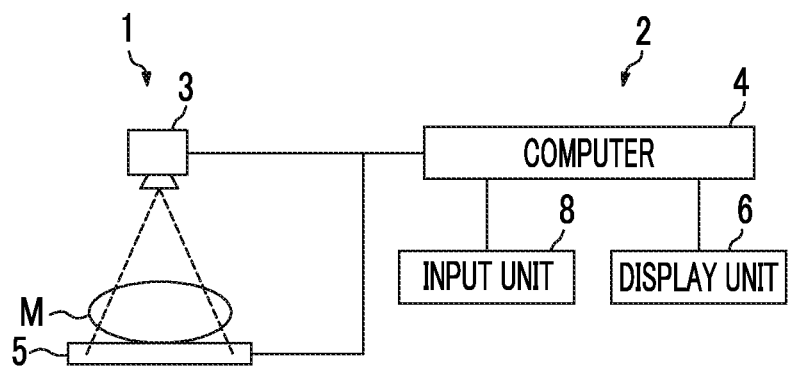
FIG. 1 is a schematic block diagram showing the configuration of a radiographic imaging system to which a radiographic image processing device according to a first embodiment of the invention is applied.

Hereinafter, an embodiment of the invention will be described referring to the drawings. FIG. 1 is a schematic block diagram showing the configuration of a radiographic imaging system to which a radiographic image processing device according to a first embodiment of the invention is applied. The radiographic image processing system according to this embodiment performs scattered radiation elimination processing for removing scattered radiation from a radiographic image of an object to improve contrast, and comprises an imaging device 1, and a control device 2 including a radiographic image processing device according to this embodiment, as shown in FIG. 1.

The imaging device 1 comprises an X-ray source 3 which irradiates an object M with X-rays, and a radiation detector 5 which detects X-rays transmitted through the object M to acquire a radiographic image of the object M. In this embodiment, a scattered radiation elimination grid for eliminating scattered radiation scattered by the object M among the X-rays transmitted through the object M is not disposed between the object M and a radiation detector 5.

For the radiation detector 5, a so-called direct radiation detector which can repeatedly record and read a radiographic image and directly receives exposure of radiation to generate electric charge may be used, or a so-called indirect radiation detector which converts radiation to visible light once and converts visible light to an electric charge signal may be used. As a system for reading a radiographic image signal, although a so-called TFT reading system in which a radiographic image signal is read by turning on or off a thin film transistor (TFT) switch, or a so-called optical reading system in which a radiographic image signal is read by exposing read light is desirably used, the invention is not limited thereto, and other systems may be used.

The radiation detector 5 is connected to the control device 2 through a cable or the like or in a wireless manner. The control device 2 is provided with a circuit board on which a detector controller which controls reading of an electric charge signal from the radiation detector 5, a charge amplifier which converts the electric charge signal read from the radiation detector 5 to a voltage signal, a correlated double sampling circuit which samples the voltage signal output from the charge amplifier, an AD conversion unit which converts the voltage signal to a digital signal, and the like are provided.

The control device 2 comprises a computer 4, and a display unit 6 and an input unit 8 connected to the computer 4.

Figure 2:
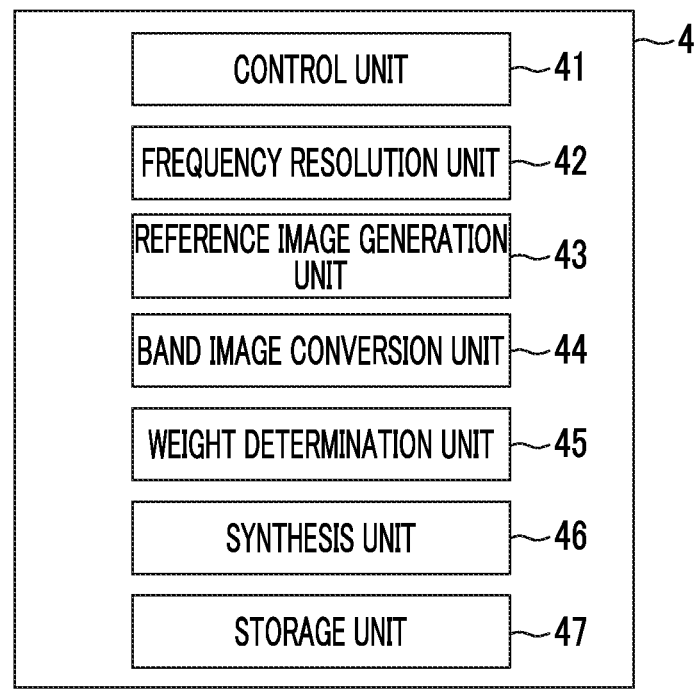
FIG. 2 is a block diagram showing the schematic internal configuration of a computer of the radiographic imaging system in the first embodiment.

The computer 4 comprises a central processing unit (CPU), a semiconductor memory, a communication interface, a storage device, such as a hard disk or a SSD, and the like, and a control unit 41, a frequency resolution unit 42, a reference image generation unit 43, a band image conversion unit 44, a weight determination unit 45, a synthesis unit 46, and a storage unit 47 shown in FIG. 2 are constituted of these kinds of hardware. The frequency resolution unit 42, the reference image generation unit 43, the band image conversion unit 44, the weight determination unit 45, and the synthesis unit 46 constitute a radiographic image processing device of the invention.

The control unit 41 outputs a predetermined control signal to the X-ray source 3 and the radiation detector 5 to control imaging, or controls the whole processing which is performed in the computer 4.

The frequency resolution unit 42 performs frequency resolution of a radiographic image G0 acquired by imaging to generate band images representing frequency components in a plurality of frequency bands.

The reference image generation unit 43 generates a reference image R0 representing information associated with scattered radiation included in the radiographic image G0 from the radiographic image G0 and generates a plurality of band reference images Rj corresponding to a plurality of frequency bands from the reference image R0.

The band image conversion unit 44 performs conversion between the corresponding pixels of the band reference images Rj and the band images in the corresponding frequency bands to generate converted band images RLj.

The weight determination unit 45 determines weights Wj to the converted band images RLj in a plurality of frequency bands.

The synthesis unit 46 synthesizes the converted band images RLj to generate a processed radiographic image G0'.

The storage unit 47 stores various kinds of information necessary for processing in the respective units.

The display unit 6 is constituted of a CRT, a liquid crystal display, or the like, and assists the radiographic image acquired by imaging and various inputs necessary for scattered radiation elimination processing described below. The input unit 8 is constituted of a keyboard, a mouse, a touch panel, and the like.

Figure 3:
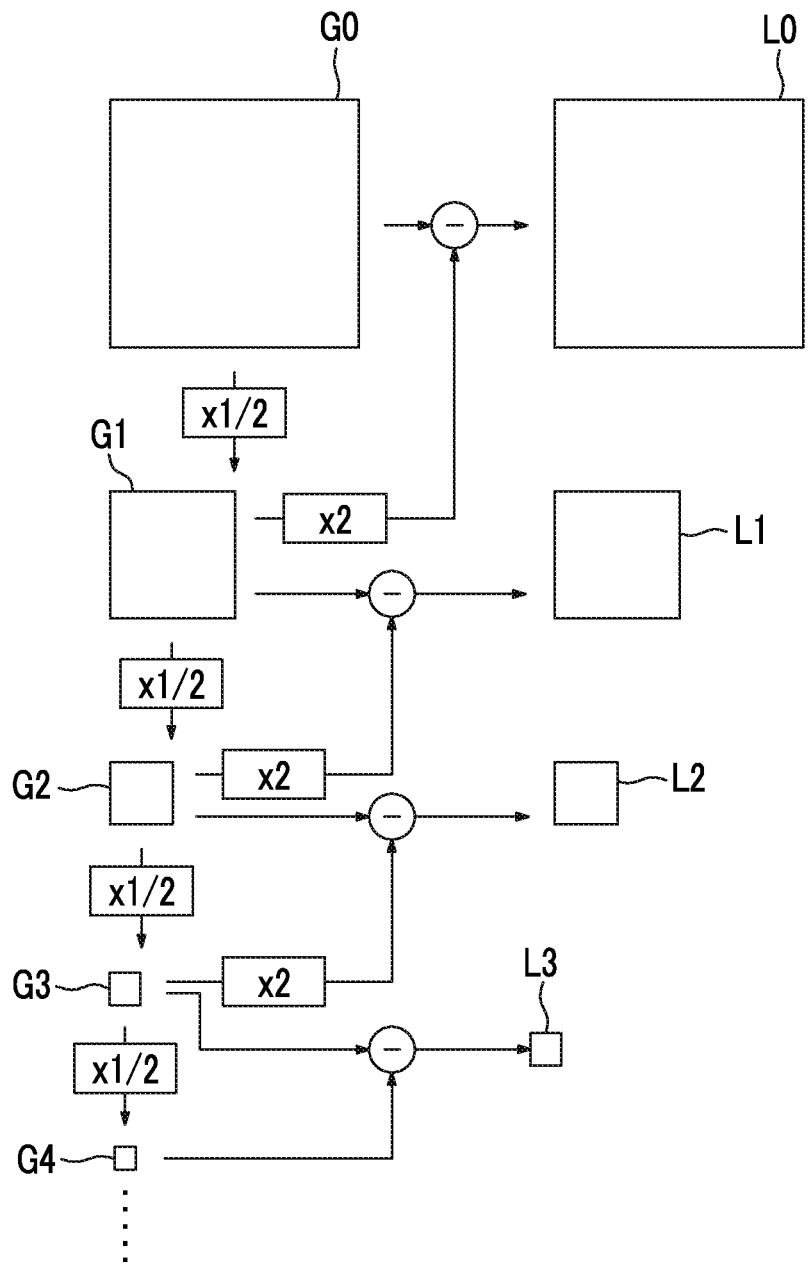
FIG. 3 is a diagram illustrating frequency resolution.

Hereinafter, the processing in the respective units will be described in detail. FIG. 3 is a diagram illustrating frequency resolution which is performed in the frequency resolution unit 42. First, the frequency resolution unit 42 performs filtering on a radiographic image G0 by, for example, a Gaussian filter of σ=1 and reduces the radiographic image G0 half to generate a reduced image G1 as a Gaussian component. The reduced image G1 is obtained by reducing the radiographic image G0 half. Next, the frequency resolution unit 42 performs interpolation calculation, such as third-order B spline interpolation, enlarges the reduced image G1 to the same size of the radiographic image G0, and subtracts the enlarged reduced image G1 from the radiographic image G0 to generate a band image L0 as a Laplacian component of the highest frequency band. In this embodiment, for convenience, the highest frequency band is referred to as the zero-th frequency band.

Next, the frequency resolution unit 42 performs filtering on the reduced image G1 by a Gaussian filter of σ=1 and reduces the reduced image G1 half to generate a reduced image G2, enlarges the reduced image G2 to the same size as the reduced image G1, and subtracts the enlarged reduced image G2 from the reduced image G1 to generate a band image L1 of a first frequency band. In addition, the processing described above is repeated until a band image of a desired frequency band is generated, thereby generating band images Lj (j=0 to n) of a plurality of frequency bands. In this embodiment, for example, the processing described above is repeated until a band image L3 of a third frequency band is obtained.

Here, the signal value of each pixel of the reduced image represents the density of the pixel, and the signal value of each pixel of the band image Lj represents the magnitude of the frequency component of the frequency band in the pixel. A plurality of band images of different frequency bands may be generated by other methods for multiple resolution conversion, such as wavelet conversion.

Next, the processing in the reference image generation unit 43 will be described. In this embodiment, the reference image generation unit 43 generates the reference image in which a scattered radiation content distribution in the radiographic image G0 is used as the pixel value of each pixel. For example, if the object M is a chest, the scattered radiation content distribution is the distribution of the content of scattered radiation in the radiographic image in which the content of scattered radiation is high in a central portion of the radiographic image where there is a mediastinum and the content of scattered radiation is low in a peripheral portion where there is a lung field.

The reference image generation unit 43 analyzes the radiographic image acquired by imaging to acquire scattered component information, that is, the scattered radiation content distribution. The analysis of the radiographic image is performed based on irradiation field information, object information, and imaging conditions at the time of imaging the radiographic image.

The irradiation field information is information representing an irradiation field distribution relating to the position and size of an irradiation field included in the radiographic image in a case where imaging is performed using an irradiation field diaphragm. The object information is information relating to the position of the object on the radiographic image, the distribution of the composition of the object, the size of the object, the thickness of the object, and the like, in addition to the type of object, such as chest, abdomen, and head. The imaging conditions are information relating to an irradiation dose (tube current×irradiation time) at the time of imaging, a tube voltage, an imaging distance (the sum of the distance between the X-ray source and the object and the distance between the object and the radiation detector), an air gap amount (the distance between the object and the radiation detector), the characteristics of the radiation detector, and the like. The irradiation field information, the object information, and the imaging conditions are factors which determine of the distribution of scattered radiation included in the radiographic image. For example, the magnitude of scattered radiation depends on the size of the irradiation field, when the thickness of the subject is great, scattered radiation increases, and if there is air between the object and the radiation detector, scattered radiation decreases. Therefore, with the use of these kinds of information, it is possible to more accurately acquire the scattered radiation content distribution. These kinds of information may be acquired by, for example, an input of an operator from the input unit 8.

The reference image generation unit 43 calculates a primary radiographic image and a scattered radiation image from a distribution $T(x,y)$ of an object thickness in the radiographic image acquired by imaging according to Expressions (1) and (2) described below, calculates a scattered radiation content distribution $S(x,y)$ from the calculated primary radiographic image and scattered radiation image based on Expression (3), and generates a reference image R0 in which the pixel value of each pixel $(x,y)$ is $S(x,y)$. The scattered radiation content distribution $S(x,y)$ takes a value of 0 to 1.

$$Ip(x,y)=Io(x,y)\times\exp(-\mu\times T(x,y)) \quad (1)$$

$$Is(x,y)=Io(x,y)*S\sigma(T(x,y)) \quad (2)$$

$$S(x,y)=Is(x,y)/(Is(x,y)+Ip(x,y)) \quad (3)$$

Here, $(x,y)$ is the coordinates of a pixel position of the radiographic image, $Ip(x,y)$ is a primary radiographic image at the pixel position $(x,y)$, $Is(x,y)$ is a scattered radiation image at the pixel position $(x,y)$, $Io(x,y)$ is an incidence dose on an object surface at the pixel position $(x,y)$, $\mu$ is a radiation attenuation coefficient of the object, and $S\sigma(T(x,y))$ is a convolution kernel which represents the characteristics of scattering according to the object thickness at the pixel position $(x,y)$. Expression (1) is an expression based on a known exponential attenuation rule, and Expression (2) is an expression based on a method described in J. M. Boon et al., "An analytical model of the scattered radiation distribution in diagnostic radiology", Med. Phys. 15(5), 1988 (Reference Document 1). The incidence dose $Io(x,y)$ on the object surface is canceled by division when calculating $S(x,y)$ even if any value is defined, and thus, may take an arbitrary value, for example, 1.

The distribution $T(x,y)$ of the object thickness may be calculated by converting the pixel value of the radiographic image G0 to the thickness with the radiation attenuation coefficient value assuming that the luminance distribution in the radiographic image G0 substantially matches the distribution of the thickness of the object. Alternatively, the thickness of the object may be measured using a sensor or the like or may be approximated by a model, such as a cube or an elliptical column.

Here, * in Expression (2) is an operator representing convolution calculation. The property of the kernel changes with the distribution of the irradiation field, the distribution of the composition of the object, the irradiation dose at the time of imaging, the tube voltage, the imaging distance, the air gap amount, the characteristics of the radiation detector, and the like, in addition to the thickness of the object. According to the method described in Reference Document 1, scattered radiation can be approximated by convolution of a point spread function (in Expression (2), $S\sigma(T(x,y))$) for primary radiation.

$S\sigma(T(x,y))$ can be experimentally determined according to the irradiation field information, the object information, the imaging conditions, and the like.

Figure 4:
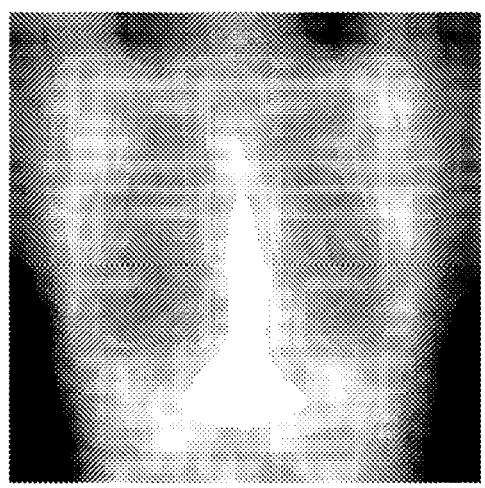
FIG. 4 is a diagram showing a scattered radiation content distribution in a radiographic image of a chest.

FIG. 4 is a diagram showing a reference image R0 in a radiographic image of a chest. In FIG. 4, when the scattered radiation content distribution $S(x,y)$ is high, luminance at each pixel position is high. From FIG. 2, it is understood that the content of scattered radiation is high in the mediastinal portion and in the periphery of the lung field in the image of the chest.

In this embodiment, although $S\sigma(T(x,y))$ may be calculated based on the irradiation field information, the object information, and the imaging conditions at the time of imaging, a table in which various kinds of irradiation field information, various kinds of object information, and various kinds of imaging conditions correspond to $S\sigma(T(x,y))$ may be stored in the storage unit 47, and $S\sigma(T(x,y))$ may be determined based on the irradiation field information, the object information, and the imaging conditions at the time of imaging with reference to the table. $S\sigma(T(x,y))$ may be approximated by $T(x,y)$.

A reference image R0 in which a body thickness distribution $T(x,y)$ of the object M, instead of the scattered radiation content distribution $S(x,y)$, is used as the pixel value of each pixel may be generated. As described above, the body thickness distribution $T(x,y)$ may be calculated by converting the pixel value of the radiographic image to the thickness with the radiation attenuation coefficient value assuming that the luminance distribution in the radiographic image substantially matches the distribution of the thickness of the object, or may be measured by a sensor. The body thickness of the object M may be estimated and a reference image R0 may be generated using the estimated body thickness. Specifically, a virtual model of the object M having a predetermined body thickness distribution may be acquired, an image in which an estimated primary radiographic image estimating a primary radiographic image obtained by imaging the virtual model through radiographic imaging from the virtual model is synthesized with an estimated scattered radiation image estimating a primary radiographic image obtained by imaging the virtual mode through radiographic imaging from the virtual model may be generated as an estimated image estimating a radiographic image acquired by imaging the object, the body thickness distribution of the virtual model may be corrected such that the difference between the estimated image and the radiographic image becomes small, and the correct body thickness distribution of the virtual model may be estimated as the body thickness distribution of the object.

Figure 5:
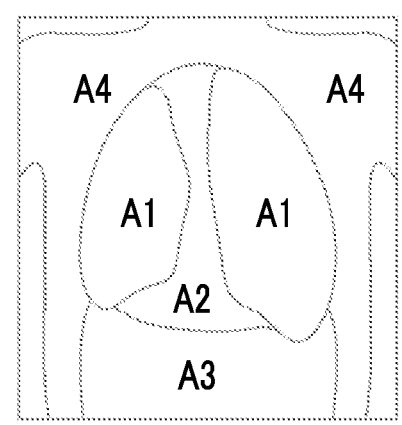
FIG. 5 is a diagram illustrating division of anatomical regions in the radiographic image of the chest.

For example, if the object M is a chest, scattered radiation is numerous in a central portion of the radiographic image where there is a mediastinum, and scattered radiation is little in a peripheral portion where there is a lung field. For this reason, the radiographic image G0 may be divided into anatomical regions, and the scattered radiation content may be set for each divided region. For example, a radiographic image of a chest shown in FIG. 5 may be divided into anatomical regions of regions A1 of a lung field, a mediastinal portion A2, an abdominal portion A3, and portions A4 other than these portions, and the scattered radiation content distribution may be set for each region.

Figure 6:
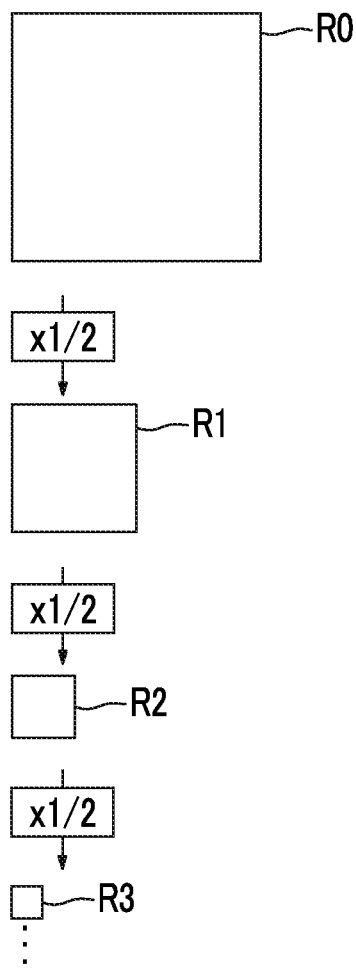
FIG. 6 is a diagram illustrating generation of band reference images in the first embodiment.

The reference image generation unit 43 generates band reference images from the reference image R0 generated in the manner described above. FIG. 6 is a diagram illustrating generation of band reference images in the first embodiment. As shown in FIG. 6, the reference image generation unit 43 performs filtering processing on the reference image R0 by, for example, a Gaussian filter of σ=1 and reduces the reference image R0 half to generate a band reference image R1. Similarly, the band reference image R1 is reduced half to generate a band reference image R2. The processing described above is repeated until the a band reference image corresponding to a desired frequency band is generated, thereby generating band reference images Rj (where j=0 to n) corresponding to a plurality of frequency bands. In this embodiment, the processing described above is repeated until a band reference image R3 corresponding to a third frequency band is obtained. Since the reference image R0 has the same size as the radiographic image G0, in the following description, the reference image R0 is referred to as a zero-th band reference image R0.

The band image conversion unit 44 performs multiplication between the corresponding pixels of the band reference images Rj and the band images Lj in the corresponding frequency bands to generate converted band images RLj. Specifically, the pixel value RLj(x,y) of each pixel of each of the converted band images RLj is calculated by Expression (4) described below.

$$RLj(x,y)=Rj(x,y) \times Lj(x,y) \quad (4)$$

The weight determination unit 45 determines weights to the converted band images RLj of the respective frequency bands. Here, scattered radiation in the radiographic image G0 is comparatively numerous in a low frequency band, and is little in a high frequency band. For this reason, the weight determination unit 45 determines weights Wj such that the weight Wj to the converted band image RLj of a low frequency band is greater than the weight to the converted band image RLj of a high frequency band. For example, in this embodiment, a weight W3 of a lowest frequency band is determined, a weight W2 of the next higher frequency band is determined to W3×0.8, a weight W1 of the next higher frequency band is determined to W2×0.8, and a weight W0 of a highest frequency band is determined to W1×0.8. The values of the weights Wj are not limited thereto.

Figure 7:
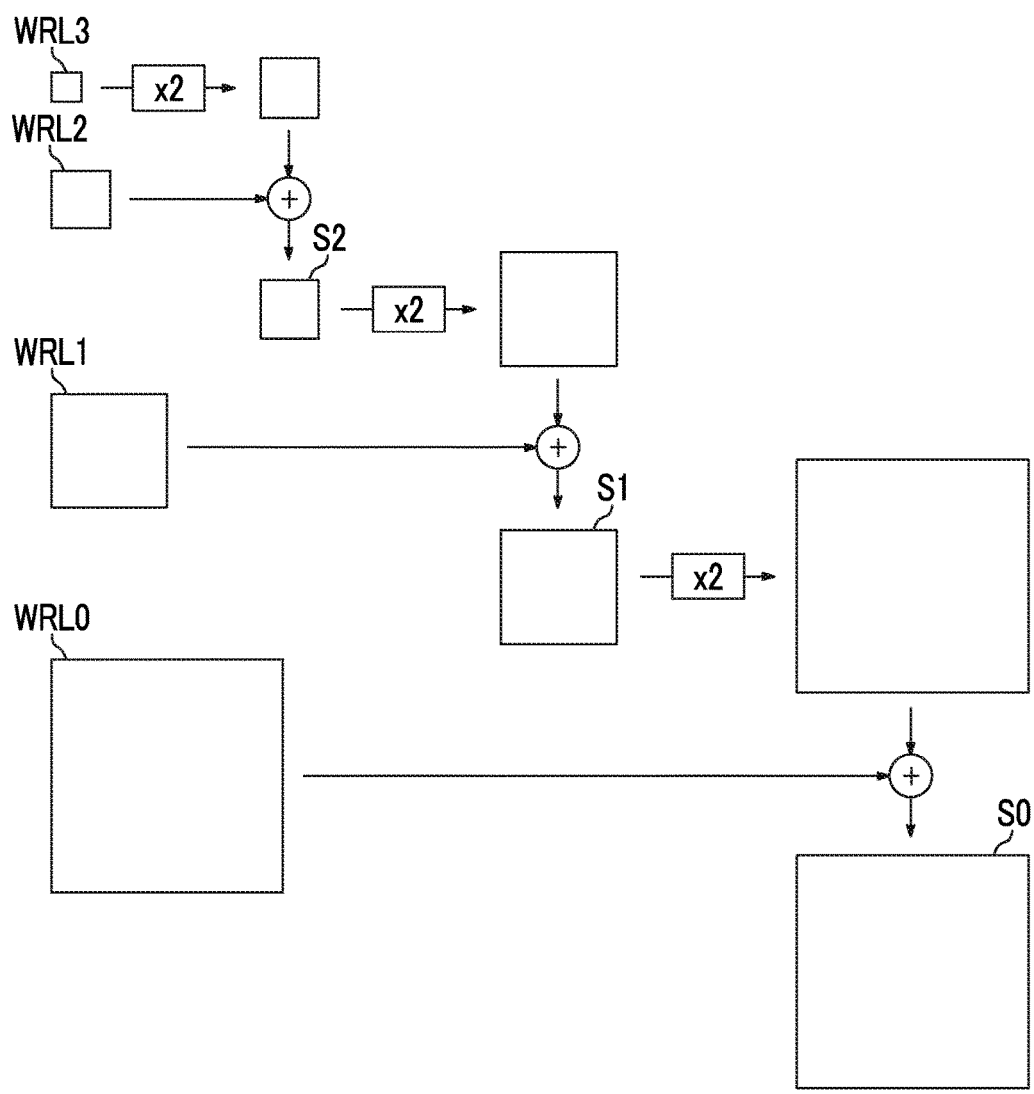
FIG. 7 is a diagram illustrating frequency synthesis.

The synthesis unit 46 multiples all pixels of the converted band images RLj by the weights Wj of the corresponding frequency bands and performs frequency synthesis of the converted band images WRLj multiplied by the weights Wj to generate a scattered radiation image S0 representing a scattered radiation component included in the radiographic image G0. FIG. 7 is a diagram illustrating frequency synthesis. In this embodiment, since the band images are generated up to the band image L3 of the third frequency band, the synthesis unit 46 enlarges a converted band image WRL3 of the third frequency band two times, and the enlarged image and a converted band image WRL2 of a second frequency band are added to generate a scattered radiation image S2. Next, the scattered radiation image S2 is enlarge two times, and the enlarged image and a converted band image WRL1 of the first frequency band are added to generate a scattered radiation image S1. The scattered radiation image S1 is enlarged two times, and the enlarged image and a converted band image WRL0 of a zero-th frequency band are added to generate a scattered radiation image S0.

The scattered radiation image S0 represents a scattered radiation component included in the radiographic image G0. For this reason, the synthesis unit 46 subtracts the scattered radiation image S0 from the radiographic image G0 between the corresponding pixels to generate a processed radiographic image G0', in which scattered radiation is eliminated.

Figure 8:
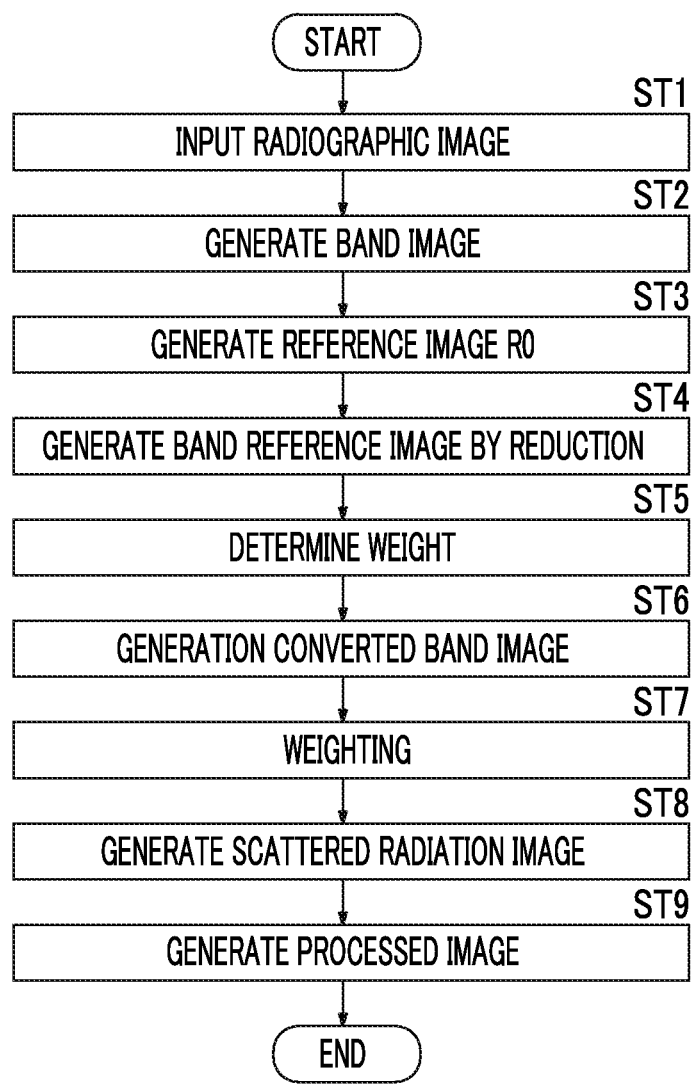
FIG. 8 is a flowchart showing processing which is performed in the first embodiment.
Figure 9:
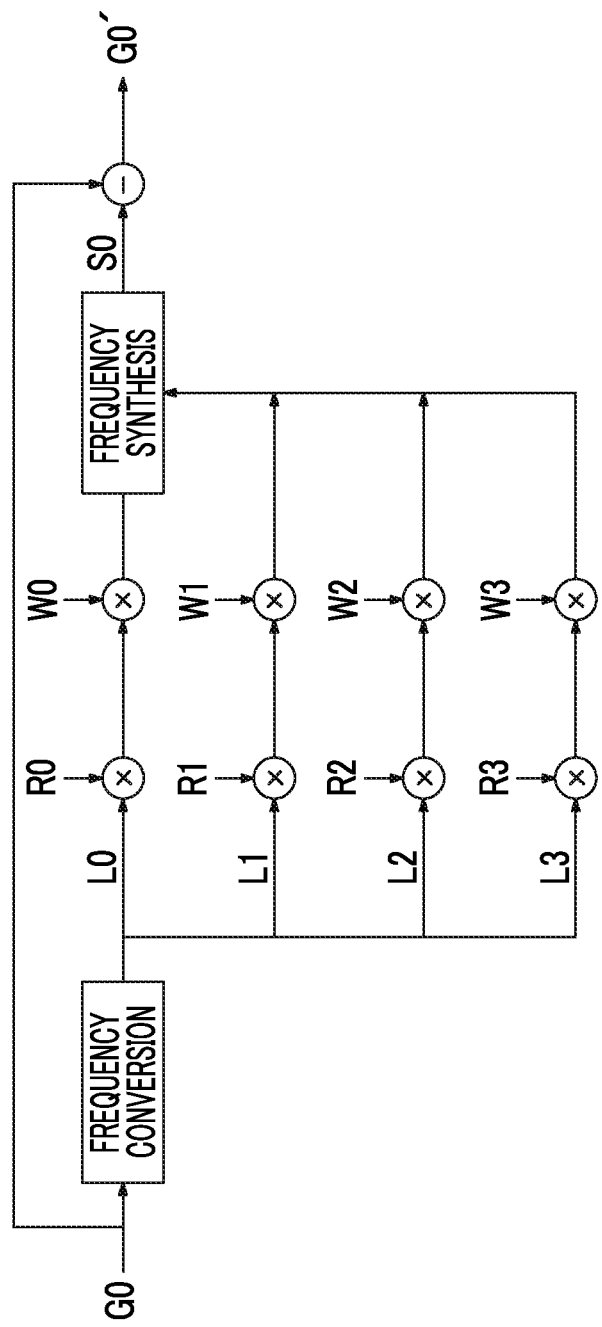
FIG. 9 is a diagram schematically showing processing which is performed in the first embodiment.

Next, processing which is performed in the first embodiment will be described. FIG. 8 is a flowchart showing processing which is performed in the first embodiment, and FIG. 9 is a diagram schematically showing processing which is performed in the first embodiment. If the radiographic image G0 acquired in the imaging device 1 is input to the computer 4 (Step ST1), the frequency resolution unit 42 performs frequency resolution of the radiographic image G0 to generate band images Lj representing frequency components in a plurality of frequency bands (Step ST2). The reference image generation unit 43 generates the reference image R0, in which the scattered radiation content distribution of the radiographic image G0 is used as the pixel value of each pixel, from the radiographic image G0 (Step ST3), and sequentially reduces the reference image R0 to generate a plurality of band reference images Rj corresponding to a plurality of frequency bands (Step ST4). The weight determination unit 45 determines the weights Wj in a plurality of frequency bands (Step ST5). Either the processing of Steps ST3 and ST4 or the processing of Step ST5 may be performed earlier, or the processing of Steps ST3 and ST4 and the processing of Step ST5 may be performed earlier than the processing of Step ST2. The processing of Step ST2, the processing of Steps ST3 and ST4, and the processing of Step ST5 may be performed in parallel.

Next, the band image conversion unit 44 performs conversion between the corresponding pixels of the band reference images Rj and the band images Lj in the corresponding frequency bands to generate the converted band images RLj (Step ST6). Then, the synthesis unit 46 performs weighting by multiplying the converted band images RLj of the respective frequency bands by the weights Wj (Step ST7), and further performs frequency synthesis of the converted band images WRLj multiplied by the weights to generate the scattered radiation image S0 (Step ST8). Then, the scattered radiation image S0 is subtracted from the radiographic image G0 to generate the processed radiographic image G0' (Step ST9), and the processing ends. The processed radiographic image is displayed on the display unit 6 and used for diagnosis, or is transmitted to and stored in an external image server.

In this way, in the first embodiment, the band images Lj are generated from the radiographic image G0, the reference image R0 representing information associated with scattered radiation included in the radiographic image G0 is generated from the radiographic image G0, a plurality of band reference images Rj corresponding to a plurality of frequency bands are generated from the reference image R0, conversion is performed between the corresponding pixels of the band reference images Rj and the band images Lj in the corresponding frequency bands to generate the converted band images RLj, and the converted band images RLj are synthesized to generate the processed radiographic image G0' with converted contrast. For this reason, it is possible to eliminate the effect of scattered radiation in each frequency band and to eliminate the effect of scattered radiation at each position on the radiographic image. Therefore, it is possible to satisfactorily improve degradation of contrast due to the effect of scattered radiation in the radiographic image.

The weights Wj to the converted band images RLj in the respective frequency bands are determined, and the processed radiographic image G0' is generated based on the converted band images WRLj weighted by the weights Wj, whereby it is possible to vary the degree of elimination of scattered radiation in the respective frequency bands; thus, it is possible to appropriately eliminate the effect of scattered radiation according to deviation in the frequency band of scattered radiation. Therefore, it is possible to more satisfactorily improve degradation of contrast due to the effect of scattered radiation in the radiographic image G0.

Next, a second embodiment of the invention will be described. In the second embodiment, the configuration of a radiographic image processing device is the same as in the first embodiment, and only processing to be performed is different; thus, detailed description of the device will not be repeated. In the first embodiment described above, the reference image R0 is generated from the radiographic image G0 and reference image R0 is sequentially reduced to generate the band reference images Rj; however, the second embodiment is different from the first embodiment in that a reference image is generated from a reduced image of a lowest frequency band and the reference image is sequentially enlarged to generate the band reference images Rj.

Figure 10:
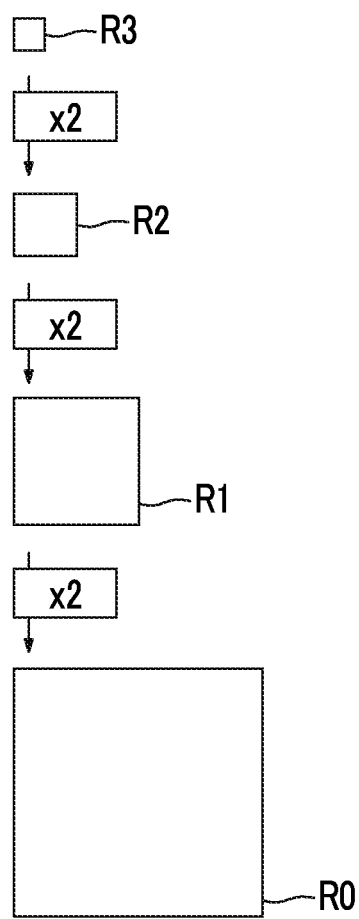
FIG. 10 is a diagram illustrating generation of band reference images in a second embodiment.

In the second embodiment, the reference image generation unit 43 performs processing as follows. FIG. 10 is a diagram illustrating generation of band reference images in the second embodiment. In this embodiment, the band images are generated by frequency resolution up to the band image L3 of the third frequency band, and the reference image generation unit 43 analyzes a reduced image G3 generated at this time similarly to the first embodiment described above to generate a reference image R3 representing the scattered radiation content distribution of the reduced image G3. The reference image generation unit 43 enlarges the reference image R3 two times to generate a band reference image R2 corresponding to the next higher frequency band. The band reference image R2 is enlarged two times to generate a band reference image R1 corresponding to the next higher frequency band. Then, the processing described above is repeated until a band reference image corresponding to a highest frequency band is generated, thereby generating band reference images Rj (where j=0 to n) corresponding to a plurality of frequency bands.

Figure 11:
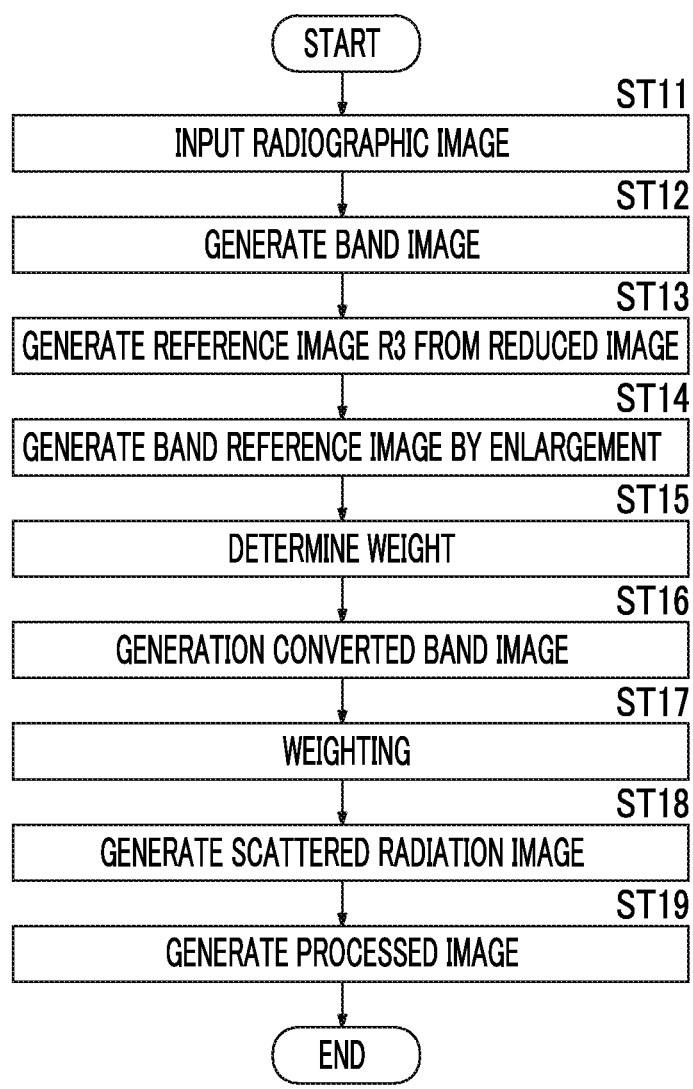
FIG. 11 is a flowchart showing processing which is performed in the second embodiment.

Next, processing which is performed in the second embodiment will be described. FIG. 11 is a flowchart showing processing which is performed in the second embodiment. If the radiographic image G0 acquired in the imaging device 1 is input to the computer 4 (Step ST11), the frequency resolution unit 42 performs frequency resolution of the radiographic image G0 to generate the band images Lj representing frequency components in a plurality of frequency bands (Step ST12). The reference image generation unit 43 generates the reference image R3, in which the scattered radiation content distribution of the reduced image G3 is used as the pixel value of each pixel, from the reduced image G3 (Step ST13), and sequentially enlarges the reference image R3 to generate a plurality of band reference images Rj corresponding to a plurality of frequency bands (Step ST14). The weight determination unit 45 determines the weights Wj in a plurality of frequency bands (Step ST15).

Next, the band image conversion unit 44 performs conversion between the corresponding pixels of the band reference images Rj and the band images Lj in the corresponding frequency bands to generate the converted band images RLj (Step ST16). Then, the synthesis unit 46 performs weighting by multiplying the converted band images RLj of the respective frequency bands by the weights Wj (Step ST17), and further performs frequency synthesis of the converted band images WRLj multiplied by the weights to generate the scattered radiation image S0 (Step ST18). Then, the scattered radiation image S0 is subtracted from the radiographic image G0 to generate the processed radiographic image G0' (Step ST19), and the processing ends.

In this way, in the second embodiment, the reference image R3 is generated from the reduced image G3, and the reference image R3 is enlarged to generate the band reference images Rj of a plurality of frequency bands. For this reason, it is possible to reduce the calculation amount for generating the band reference images Rj compared to a case where the reference image R0 is generated from the radiographic image G0 as in the first embodiment, and as a result, it is possible to generate the reference image and the band reference image at high speed.

In the band reference images Rj generated in the second embodiment, the accuracy of the scattered radiation content distribution is slightly deteriorated compared to the band reference images Rj generated by reducing the reference image R0 generated from the radiographic image G0 as in the first embodiment. However, the inventors have conducted functional evaluation on the processed radiographic image and have confirmed that, in the processed radiographic image G0' generated using the band reference images Rj of the second embodiment, the effect of scattered radiation is eliminated without being inferior to the processed radiographic image G0' generated using the band reference images Rj of the first embodiment.

Next, a third embodiment of the invention will be described. In the third embodiment, the configuration of the radiographic image processing device is the same as in the first embodiment, and only processing to be performed is different; thus, detailed description of the device will not be repeated. In the first embodiment described above, the image representing the scattered radiation content distribution included in the radiographic image G0 is generated as the reference image representing information associated with scattered radiation; however, the third embodiment is different from the first embodiment in that an image representing a primary radiation content distribution of the radiographic image G0 is generated as a reference image.

Here, the radiographic image G0 has a scattered radiation image and a primary radiographic image. As described above, the scattered radiation content distribution $S(x,y)$ takes a value of 0 to 1. Accordingly, a primary radiation content distribution P(x,y) in the radiographic image G0 can be calculated by 1−S(x,y). In the third embodiment, the reference image generation unit 43 calculates the scattered radiation content distribution S(x,y) as in the first embodiment, performs calculation of 1−S(x,y) to calculate the primary radiation content distribution P(x,y), and generates a reference image (represented by PR0 in order to distinguish from R0) in which the pixel value of each pixel is P(x,y).

On the other hand, scattered radiation included in the radiographic image is comparatively numerous in a low frequency band and is little in a high frequency band. For this reason, primary radiation is comparatively numerous in a high frequency band and is little in a low frequency band. Accordingly, in the third embodiment, the weight determination unit 45 determines weights (represented by PWj) such that a weight to a converted band image (represented by PRLj) of a high frequency band is greater than a weight to a converted band image RLj of a low frequency band. For example, in this embodiment, a weight PW0 of a highest frequency band is determined, a weight PW1 of the next lower frequency band is determined to PW0×0.8, a weight PW2 of the next lower frequency band is determined to PW1×0.8, and a weight PW3 of a lowest frequency band is determined to PW2×0.8. The values of the weights PWj are not limited thereto.

Figure 12:
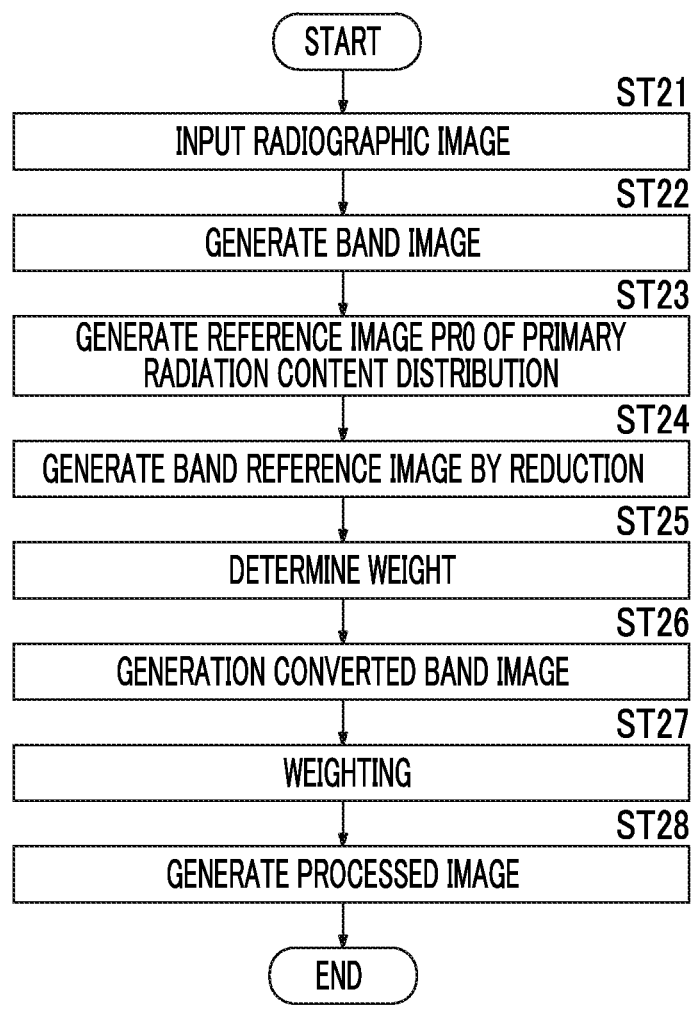
FIG. 12 is a flowchart showing processing which is performed in a third embodiment.
Figure 13:
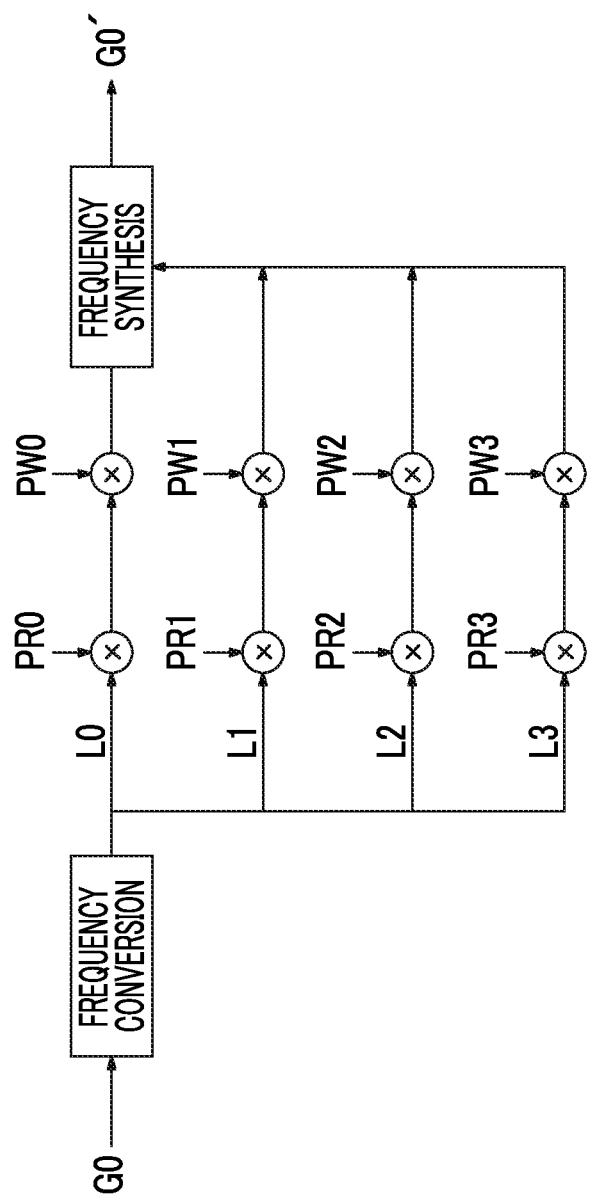
FIG. 13 is a diagram schematically showing processing which is performed in the third embodiment.

Next, processing which is performed in the third embodiment will be described. FIG. 12 is a flowchart showing processing which is performed in the third embodiment, and FIG. 13 is a diagram schematically showing processing which is performed in the third embodiment. If the radiographic image G0 acquired in the imaging device 1 is input to the computer 4 (Step ST21), the frequency resolution unit 42 performs frequency resolution of the radiographic image G0 to generate the band images Lj representing frequency components in a plurality of frequency bands (Step ST22). The reference image generation unit 43 generates the reference image PR0 in which the primary radiation content distribution of the radiographic image G0 is used as the pixel value of each pixel (reference image generation of primary radiation content distribution: Step ST23), and sequentially reduces the reference image PR0 to generate a plurality of band reference images Rj corresponding to a plurality of frequency bands (Step ST24). The weight determination unit 45 determines the weights PWj in a plurality of frequency bands (Step ST25).

Next, the band image conversion unit 44 performs conversion between the corresponding pixels of the band reference images PRj and the band images Lj in the corresponding frequency bands to generate the converted band images PRLj (Step ST26). Then, the synthesis unit 46 performs weighting by multiplying the converted band images PRLj of the respective frequency bands by the weights PWj (Step ST27). Here, the converted band images PRLj represent the components of primary radiation in the band images Lj. Accordingly, in the third embodiment, frequency synthesis of the converted band images WPRLj multiplied by the weights is performed to generate the processed radiographic image G0' (Step ST28), and the processing ends.

In the third embodiment described above, although the reference image PR0 is generated from the radiographic image G0 and the reference image PR0 is sequentially reduced to generate the band reference images PRj, as in the second embodiment, a reference image in which the primary radiation content distribution is used as the pixel value of each pixel may be generated from a reduced image of a lowest frequency band, and the reference image may be sequentially enlarged to generate the band reference images PRj.

Figure 14:
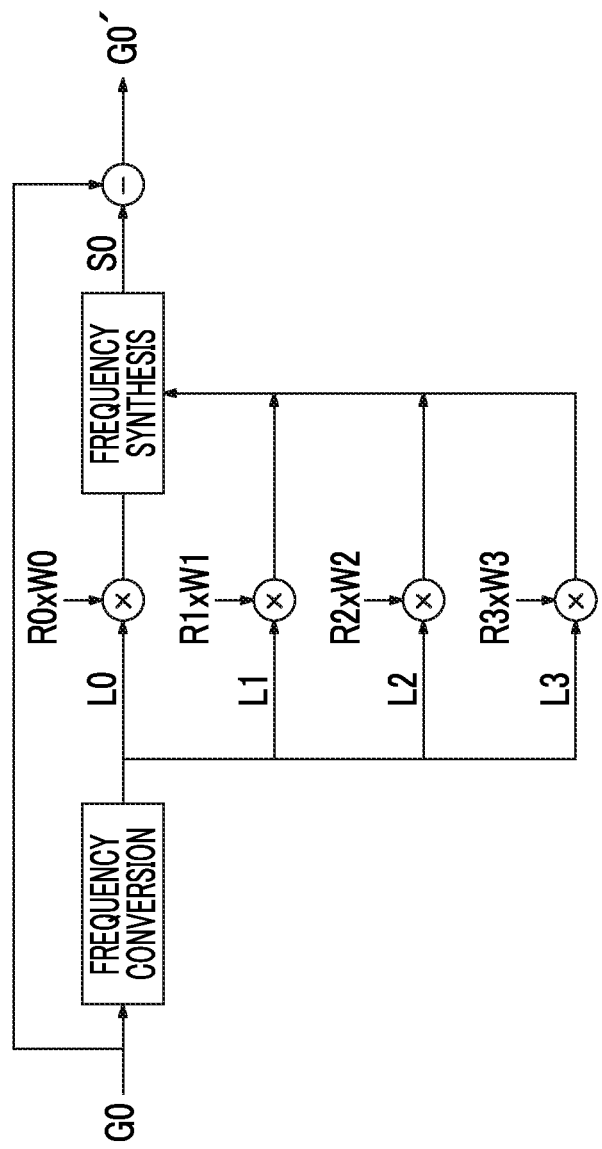
FIG. 14 is a diagram schematically showing processing which is performed in a fourth embodiment.

In the first to third embodiments, although the converted band images RLj or PRLj are multiplied by the weights Wj or PWj, the band reference images Rj or PRj may be multiplied by the weights Wj or PWj, and the band images Lj may be multiplied by band reference images WRj or WPRj multiplied by the weights Wj or PWj to generate converted band images WRLj or WPRLj. Processing in a case where this processing is applied to the first embodiment is schematically shown in FIG. 14 as a fourth embodiment.

Figure 15:
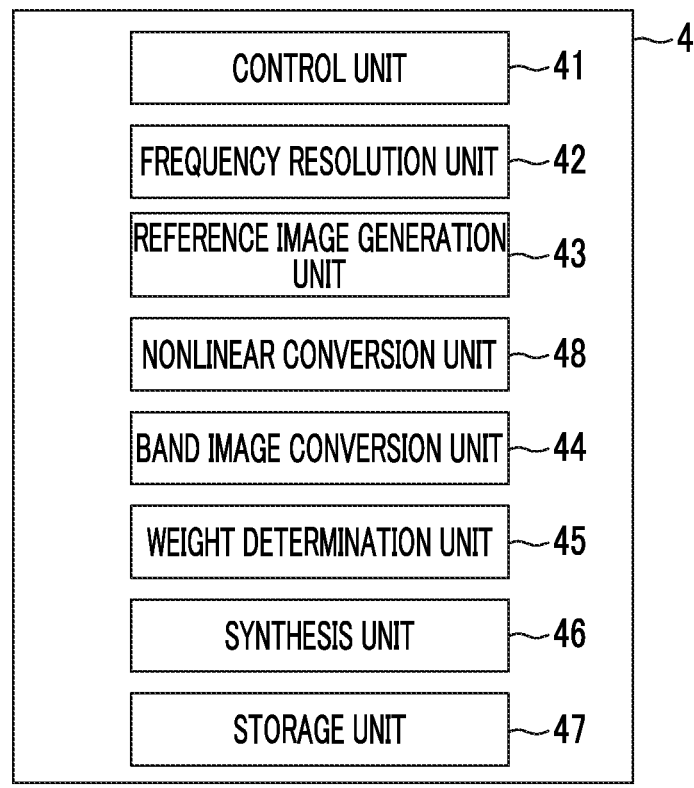
FIG. 15 is a block diagram showing the schematic internal configuration of a computer of a radiographic imaging system in a fifth embodiment.

In the first to fourth embodiments described above, the band images may be converted with a nonlinear function, and conversion may be performed between the corresponding pixels of the band reference images and the converted band images to generate converted band images. Hereinafter, this will be described as a fifth embodiment. FIG. 15 is a block diagram showing the schematic internal configuration of a computer of a radiographic imaging system in the fifth embodiment. In FIG. 15, the same configurations as those in FIG. 2 are represented by the same reference numerals, and detailed description thereof will not be repeated. The fifth embodiment is different from the first embodiment in that the radiographic imaging system comprises a nonlinear conversion unit 48 which nonlinearly converts the band images Lj.

Figure 16:
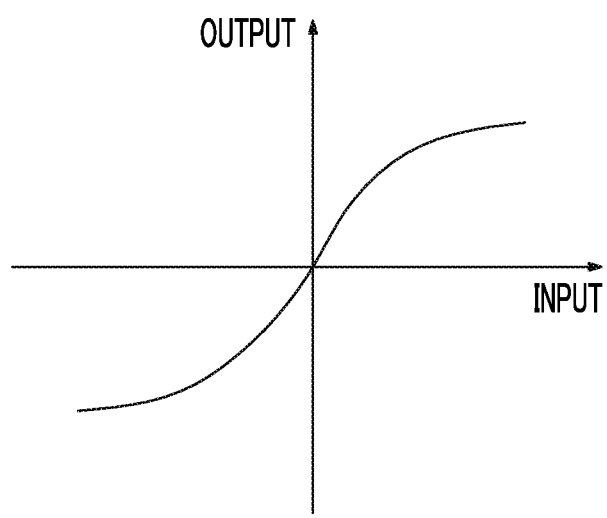
FIG. 16 is a diagram showing an example of a nonlinear function.

In the fifth embodiment, for example, as shown in FIG. 16, a nonlinear function which linearly converts a comparatively small pixel value with a predetermined inclination and converts a great pixel value so as to suppress the value of the pixel value is stored in the storage unit 47. The nonlinear function may be prepared in each frequency band. In this case, for example, as described in JP2001-218058A, the nonlinear function has a small inclination in a low frequency band.

In the fifth embodiment, the nonlinear conversion unit 48 converts the band images Lj with the nonlinear function, and the band image conversion unit 44 performs conversion between the corresponding pixels of the band reference images Rj and the band images Lj converted with the nonlinear function to generate the converted band images RLj. Then, as in the first embodiment described above, frequency synthesis of the converted band images RLj is performed to generate the processed radiographic image G0'.

In this way, the band images Lj are converted with the nonlinear function, and conversion is performed between the corresponding pixels of the band reference images Rj and the converted band images Lj to generate the converted band images RLj, whereby it is possible to improve contrast of the processed radiographic image G0'. As shown in FIG. 16, the nonlinear function for suppressing the value of a great pixel value is used, whereby it is possible to prevent contrast of the processed radiographic image G0' from being too high, and thus, to obtain the processed radiographic image G0' with higher image quality.

In particular, as in the second embodiment, in a case where the band reference images Rj in which the accuracy of the scattered radiation content distribution is slightly deteriorated are used, the band image Lj is nonlinearly converted, whereby it is possible to suppress overcorrection of scattered radiation due to degradation of the accuracy of the scattered radiation content distribution, and thus, to obtain the processed radiographic image G0' with higher image quality.

In the first to fifth embodiments described above, although the scattered radiation elimination processing is performed on the radiographic image acquired through imaging without using a grid, a radiographic image acquired through imaging using a grid may be subjected to the scattered radiation elimination processing. In this case, processing for eliminating a stripe pattern due to the grid is performed on the radiographic image, and then, the scattered radiation elimination processing is performed. Here, if the type (a lattice density, a difference of a material to be used) of scattered radiation elimination grid is different, the scattered radiation content in each frequency band changes. For this reason, in the scattered radiation elimination processing, a radiographic image (first grid used image) captured using a first grid as a desired grid may be acquired, virtual grid characteristics corresponding to a desired virtual grid may be acquired, and weights Wj to converted band images RLj calculated from the first grid used image may be converted so as to become weights Wj corresponding to a grid corresponding to the acquired virtual grid characteristics. Either the first grid or the grid corresponding to the virtual grid characteristics may have a greater scattered radiation elimination effect, and may be arbitrarily selected according to the purpose or situation. As the processing for eliminating a stripe pattern due to a grid, for example, a method described in JP2012-203504A is available.

The processed radiographic image acquired in this embodiment may be subjected to the scattered radiation elimination processing in this embodiment. In this case, the weights Wj to the converted band images RLj calculated from the processed radiographic image may be converted so as to become the weights Wj corresponding to the grid corresponding to the desired grid characteristics. In this case, either the processing for the original radiographic image or the processing for the processed radiographic image may have a greater scattered radiation elimination effect, and may be arbitrarily selected according to the purpose or situation.

Though such processing, based on a radiographic image using a grid having a grid ratio of 3:1 (or a processed radiographic image obtained by subjecting a radiographic image captured with no grid to the scattered radiation elimination processing), it is possible to virtually acquire a processed radiographic image as if captured using a grid having a grid ratio of 10:1 different from the used grid. Conversely, based on a radiographic image captured using a grid having a grid ratio of 10:1 (or a processed radiographic image obtained by subjecting a radiographic image captured with no grid to the scattered radiation elimination processing), it is possible to virtually acquire a processed radiographic image as if captured using a grid having a grid ratio of 3:1 different from the used grid. In these cases, even if imaging of the object is not repeated, it is possible to easily acquire a radiographic image with a grid ratio converted; thus, it is possible to obtain a processed radiographic image subjected to the scattered radiation elimination processing using a grid having a desired grid ratio from a radiographic image or a processed radiographic image captured at an unintended grid ratio. For this reason, it is possible to respond a demand for observing a processed radiographic image subjected to the scattered radiation elimination processing at a different degree without re-imaging the object.

On the other hand, there is a case where imaging is performed depending on an imaging region without using a scattered radiation elimination grid. It is not preferable that the scattered radiation elimination processing of the first to third embodiments described above is performed on a radiographic image acquired by imaging such a region. For this reason, it is preferable that the on/off of the scattered radiation elimination processing of this embodiment is switched depending on the imaging region. Information of the imaging region may be acquired by an input of an operator or may be automatically acquired from an imaging request input to a known console PC (not shown) which controls an imaging flow, or information which is stored in the system together with a radiographic image after imaging may be used. In a case where such information cannot be acquired, information may be acquired by performing region recognition processing on a radiographic image. In this case, a table in which the on/off of the processing corresponds to regions may be stored in the storage unit 47, and the on/off of the processing may be switched with reference to the table.

In the first to fifth embodiments described above, both of the processed radiographic image and the radiographic image before processing may be displayed, and either radiographic image for use in diagnosis may be selected.

In order to diagnose a state of heating or process of an illness, there is a case where time-dependent comparative observation is performed using a previous radiographic image. In such a case, in a case of comparing a radiographic image (referred to as a first radiographic image) acquired through imaging without using a scattered radiation elimination grid with a radiographic image (referred to as a second radiographic image) acquired through imaging using a scattered radiation elimination grid, it is preferable that the conditions for the scattered radiation elimination processing of this embodiment according to processing conditions when processing for eliminating a stripe pattern due to a grid is performed on the first radiographic image, and the image qualities of the first and second radiographic images match each other.

In the first to fifth embodiments described above, although the scattered radiation elimination processing is performed using a radiographic image acquired in the imaging device 1 which captures a radiographic image of an object using the radiation detector 5, the invention can be of course applied to a case where a radiographic image acquired by storing and recording radiographic image information of an object in a storage phosphor sheet as a radiation detector described in JP1996-266529A (JP-H08-266529A), JP1997-024039A (JP-H09-024039A), or the like and photoelectrically reading the radiographic image information from the storage phosphor sheet is used.

What is claimed is:
1. A radiographic image processing device comprising:
a frequency resolution unit for performing frequency resolution of a radiographic image captured by irradiating an object with radiation to generate band images representing frequency components in a plurality of frequency bands;
a reference image generation unit for generating a reference image representing information associated with scattered radiation included in the radiographic image from the radiographic image and generating a plurality of band reference images corresponding to the plurality of frequency bands from the reference image;
a band image conversion unit for performing conversion between the corresponding pixels of the band reference images and the band images in the corresponding frequency bands to generate converted band images; and a synthesis unit for synthesizing the converted band images to generate a processed radiographic image with converted contrast.

2. The radiographic image processing device according to claim 1,
wherein the reference image is at least one of an image representing a body thickness distribution of the object, an image representing a scattered radiation content distribution of the radiographic image, an image representing a scattered radiation content according to an anatomical region included in the radiographic image, or an image representing a primary radiation content distribution of the radiographic image.

3. The radiographic image processing device according to claim 1,
wherein the reference image generation unit generates a lowest frequency band reference image corresponding to the band image of a lowest frequency band and sequentially enlarging the lowest frequency band reference image to generate band reference images of the plurality of frequency bands including the lowest frequency band reference image.

4. The radiographic image processing device according to claim 1, further comprising:
a weight determination unit for determining weights to the converted band images in the plurality of frequency bands,
wherein the synthesis unit generates the processed radiographic image based on the converted band images weighted by the weights.

5. The radiographic image processing device according to claim 4,
wherein the synthesis unit assigns the converted band images with the weights and synthesizes the weighted converted band images to generate the processed radiographic image.

6. The radiographic image processing device according to claim 4,
wherein the band image conversion unit assigns the band reference images with the weights.

7. The radiographic image processing device according to claim 1, further comprising:
a nonlinear conversion unit for converting the band images with a nonlinear function,
wherein the band image conversion unit performs conversion between the corresponding pixels of the band reference images and the converted band images to generate the converted band images.

8. A radiographic image processing device comprising:
a frequency resolution unit for performing frequency resolution of a radiographic image captured by irradiating an object with radiation to generate band images representing frequency components in a plurality of frequency bands;
a reference image generation unit for generating a reference image representing a primary radiation content distribution included in the radiographic image from the radiographic image and generating a plurality of band reference images corresponding to the plurality of frequency bands from the reference image;
a band image conversion unit for performing conversion between the corresponding pixels of the band reference images and the band images in the corresponding frequency bands to generate converted band images; and
a synthesis unit for synthesizing the converted band images to generate a processed radiographic image with converted contrast.

9. A radiographic image processing method comprising:
performing frequency resolution of a radiographic image captured by irradiating an object with radiation to generate band images representing frequency components in a plurality of frequency bands;
generating a reference image representing information associated with scattered radiation included in the radiographic image from the radiographic image and generating a plurality of band reference images corresponding to the plurality of frequency bands from the reference image;
performing conversion between the corresponding pixels of the band reference images and the band images in the corresponding frequency bands to generate converted band images; and
synthesizing the converted band images to generate a processed radiographic image with converted contrast.

10. A non-transitory recording medium having recorded thereon a radiographic image processing program which causes a computer to execute:
a procedure for performing frequency resolution of a radiographic image captured by irradiating an object with radiation to generate band images representing frequency components in a plurality of frequency bands;
a procedure for generating a reference image representing information associated with scattered radiation included in the radiographic image from the radiographic image and generating a plurality of band reference images corresponding to the plurality of frequency bands from the reference image;
a procedure for performing conversion between the corresponding pixels of the band reference images and the band images in the corresponding frequency bands to generate converted band images; and
a procedure for synthesizing the converted band images to generate a processed radiographic image with converted contrast.

* * * * *